US00PP28241P2

(12) United States Plant Patent
Van Dijk

(10) Patent No.: US PP28,241 P2
(45) Date of Patent: Aug. 1, 2017

(54) ***ANTHURIUM* PLANT NAMED 'ANTHERBI'**

(50) Latin Name: ***Anthurium andreanum* L.**
Varietal Denomination: ANTHERBI

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 14/999,805

(22) Filed: Jun. 29, 2016

(51) Int. Cl.
*A01H 5/02* (2006.01)

(52) U.S. Cl.
USPC ..... Plt./369

(58) Field of Classification Search
USPC ..... Plt./369
See application file for complete search history.

(56) References Cited

PUBLICATIONS

PLUTO Plant Variety Databse May 12, 2017. p. 1.*

* cited by examiner

*Primary Examiner* — Annette Para
(74) *Attorney, Agent, or Firm* — Jondle & Associates, P.C.

(57) ABSTRACT

A new and distinct *Anthurium* plant named 'ANTHERBI' particularly distinguished by having shiny, bright red, orbicular cordate and very durable spathes that retain the original color for a very long period of time, dark green and long elliptical cordate, durable leaves, white spadix with yellow-orange tips, early and rich flowering continuously throughout the year and a plant height of 38.0 cm to 42.0 cm, is disclosed.

3 Drawing Sheets

Genus and species: *Anthurium andreanum* L.
Variety denomination 'ANTHERBI'.

BACKGROUND OF THE NEW PLANT

The present invention comprises a new and distinct variety of *Anthurium*, botanically known as *Anthurium andreanum* L., and hereinafter referred to by the variety name 'ANTHERBI'. This new *Anthurium* plant is a product of a planned breeding program conducted by the inventor in Bleiswijk, The Netherlands. The objective of this breeding program was to create a new, 38.0 cm to 42.0 cm height plant with shiny, bright red, orbicular cordate and very durable spathes.

The new variety originated from a cross-pollination made in April 2008 in Bleiswijk, The Netherlands. The female parent was a red *Anthurium* pot plant designated '8477-05' (unpatented), and the male parent was an orange *Anthurium* pot plant designated '6970-01' (unpatented).

A single plant was selected from the progeny of the stated cross in March 2010 and has been asexually reproduced repeatedly by tissue culture in Bleiswijk, The Netherlands over a 6-year period. The present invention has been found to retain its distinctive characteristics through successive asexual propagations.

Plant Breeder's Rights for this variety have been applied for in the European Union on Nov. 6, 2014. 'ANTHERBI' has not been made publicly available or sold anywhere in the world more than one year prior to the filing of this application.

SUMMARY OF THE INVENTION

The following are the most outstanding and distinguishing characteristics of this new variety when grown under normal horticultural practices in Bleiswijk, The Netherlands:

1) Shiny, bright red, orbicular-cordate spathe;
2) White spadix with yellow tip;
3) Green elliptical cordate leaves; and
4) Hardly any pollen production.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 34-week old plant grown in a greenhouse in Bleiswijk, The Netherlands in February 2016. Colors in the photographs may differ from the color values cited in the detailed botanical description, which accurately describe the actual colors of the new variety.

DESCRIPTION OF THE NEW VARIETY

Figure 1:
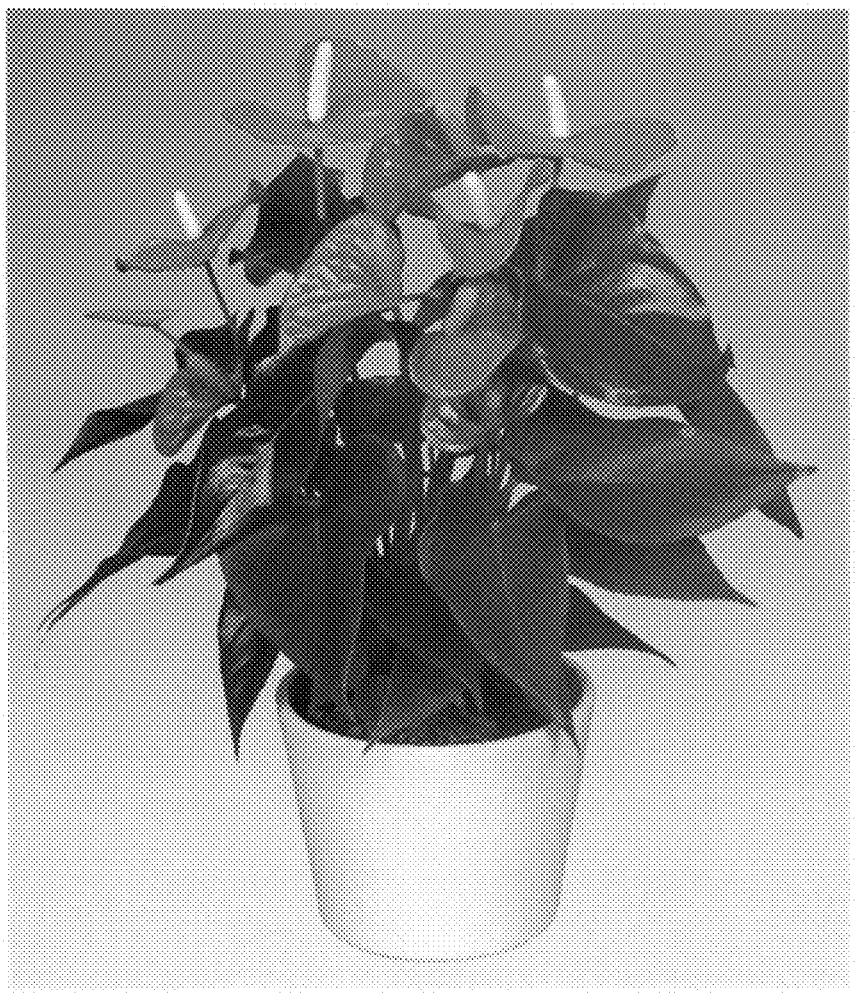
FIG. 1 shows the overall plant habit, including blooms and foliage.
Figure 2:
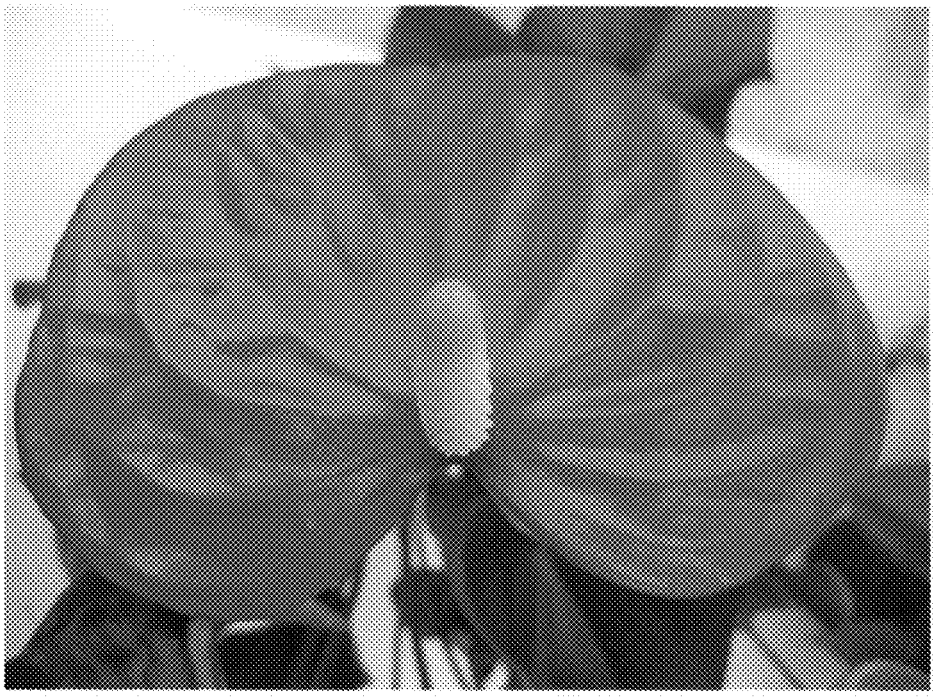
FIG. 2 shows a close-up of the mature spathe.
Figure 3:
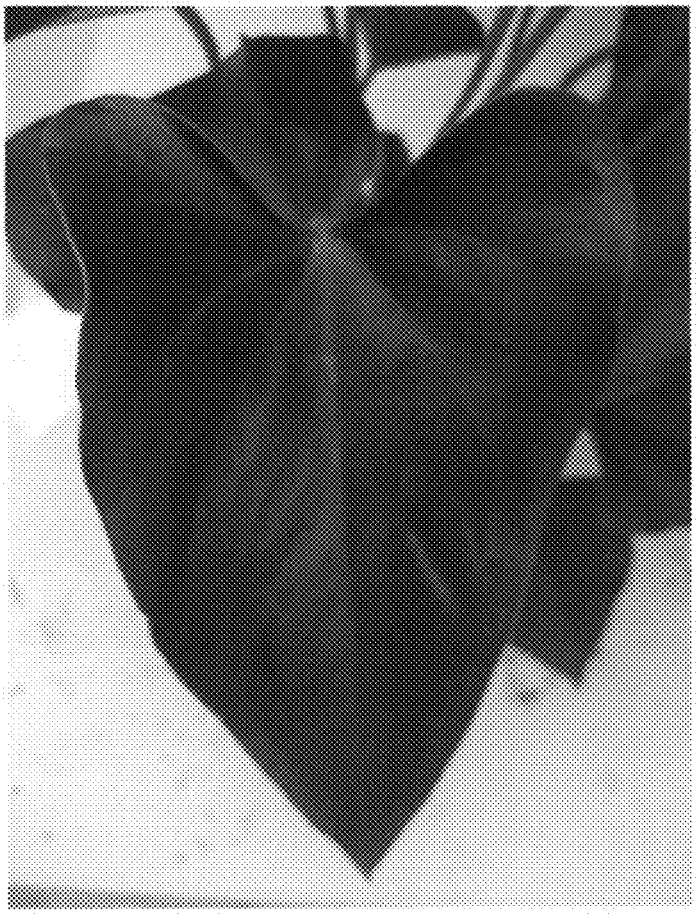
FIG. 3 shows the upper leaf blade surface.

The following detailed description sets forth the distinctive characteristics of 'ANTHERBI'. The data which define these characteristics were collected from asexual reproductions carried out in Bleiswijk, The Netherlands. The plant history was taken on 34-week old plants which were planted from tissue culture in 12-centimeter (diameter) pots and grown in a glass greenhouse between 19° C. and 24° C. Observations were made in February 2016. Color readings were taken under 5000 lux natural light in the greenhouse.

Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andreanum* L.

*Common name*.—*Anthurium*.

*Demonimation*.—'ANTHERBI'.

Parentage:

*Female parent*.—*Anthurium* plant '8477-05' (unpatented).

*Male parent*.—*Anthurium* plant '6970-01' (unpatented).

Plant:

*Propagation*.—Tissue culture (meristem).

*Root description*.—Fleshy-creamy white colored roots with small hairy lateral roots having yellow colored root tips.

*Time to produce a finished flowering plant*.—30 to 35 weeks after planting in a 12-cm (diameter) pot.

*Growth habit*.—Herbaceous perennial.

*Height* (*measured from soil, including inflorescence*).—38.0 cm to 42.0 cm.

*Width* (*measured from leaf tips*).—36.0 cm to 40.0 cm.

Leaves:

*Immature leaves*.—Length: 13.0 cm to 15.0 cm. Width: 8.0 cm to 10.0 cm. Color: Upper surface: RHS 146A. Lower surface: RHS 146B. Texture (both upper and lower surfaces): Shiny.

*Mature leaves*.—Length (fully expanded): 15.0 cm to 17.0 cm. Width: 8.0 cm to 10.0 cm. Shape: Elliptical cordate. Apex: Acuminate. Base: Cordate. Leaf blade angle with the petiole: Between 90 degrees and 105 degrees. Leaf margin: Entire. Color: Upper surface: RHS 147A. Lower surface: RHS 146B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 147B. Lower surface: RHS 146C.

*Lobes*.—Arrangement: Leaf blade has two lobes extending past the petiole. The lobes are non-touching. Length of lobes of mature leaf blades: 2.0 cm to 2.5 cm. Width of lobes of mature leaf blades: 3.5 cm to 4.5 cm. Distance from petiole/leaf junction to highest point on lobes of mature leaf blades: 2.5 cm to 3.5 cm.

*Petiole*.—Cross-section: Round. Diameter: 0.3 cm to 0.35 cm. Length: 18.0 cm to 21.0 cm for a mature leaf size. Color: Mature leaf: RHS 144A. Immature leaf: RHS 144A. Cataphyll color surrounding the petiole: Outside: RHS 145A and 181B towards the apex. Inside: RHS 145B and 181C towards the apex.

*Geniculum*.—Length: 1.5 cm to 2.0 cm. Width: 0.37 cm to 0.42 cm. Color: RHS 144A.

Inflorescence:

*Arrangement*.—Single.

*Flowering habit* (*length of flowering season*).—Continuous.

*Number of inflorescences per plant*.—7 to 10.

*Fragrance*.—Absent.

*Longevity of inflorescence on plant*.—Over half a year.

Spathe:

*Buds*.—The spathe is tightly rolled around the spadix and extrudes from the peduncle sheath. After the spathe is fully open the peduncle elongates some extra centimeters.

*Arrangement*.—Spathe angle with the peduncle is between 95 degrees and 105 degrees; the spathe stands on a wiry peduncle about 7.0 cm to 9.0 cm above the foliage.

*Shape*.—Orbicular-cordate.

*Apex*.—Mucronate.

*Base*.—Cordate.

*Texture*.—Shiny and blistered.

*Margin*.—Entire.

*Size*.—Length: 7.5 cm to 8.5 cm. Width: 8.5 cm to 9.5 cm.

*Lobes*.—Arrangement: The spathe has two lobes extending past the peduncle. The lobes are non-touching. Length: 1.0 cm to 2.0 cm. Width: 4.0 cm to 4.5 cm.

*Color*.—Just fully open: Upper surface: RHS 45B. Lower surface: RHS 45C. This red color remains for a very long period, at least more than 20 weeks after opening, although after some weeks, the base of the spathe turns to brown red.

Peduncle:

*Shape*.—Erect.

*Cross-section*.—Round.

*Length*.—30.0 cm to 33.0 cm.

*Diameter*.—0.31 cm to 0.36 cm.

*Color*.—RHS 144B.

Flowering time:

*General*.—One small rooted untreated tissue culture plant of 8.0 cm tall will flower, depending on the season, after 7 to 8 months, and 4 to 6 blossoms will appear. More blossoms appear after some additional weeks so that a full flowering and commercial plant will have 6 to 8 red spathes. Smaller blossoms may occur on immature plants.

Spadix:

*Size*.—Length: 2.8 cm to 3.3 cm (depending on spathe size). Width (at apex): 0.5 cm to 0.6 cm. Width (at base): 0.6 cm to 0.7 cm.

*Shape*.—Columnar.

*Angle from spadix tip to peduncle*.—165 to 180 degrees.

*Texture*.—When the spathe is unfurling the spadix is smooth. When the spadix matures, small stigmata protrude. The stigmata are evenly distributed round the spadix. The spadix matures from base to top, slowly giving the spadix a somewhat rough appearance.

*Color*.—Immature: RHS 15A. Mature: RHS 155B. Aged: RHS N144A.

Flowers:

*Quantity per spadix*.—150 to 200.

*Spadix flower arrangement*.—Bisexual, rounded in cross-section.

*Shape*.—Rounded.

*Size*.—Length: 0.05 cm to 0.1 cm. Diameter (maximum): 0.1 cm.

*Color*.—RHS 156D.

Reproductive organs:

*Stamens*.—Not visible.

*Pollen amount*.—None.

*Pistil*.—Quantity: Many. Length: Less than 0.01 cm. Color: RHS 156D.

*Style*.—Not observed.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed.

Disease and pest resistance: None observed.

COMPARISON WITH PARENTAL AND COMMERCIAL VARIETIES

'ANTHERBI' differs from the female parent plant '8477-05' (unpatented) in that 'ANTHERBI' has darker colored immature leaves than the immature leaves of '8477-05'.

'ANTHERBI' differs from the male parent plant '6970-01' (unpatented) in that 'ANTHERBI' has immature leaves with green lower surfaces and acuminate shaped leaf tips, whereas '6970-01' has immature leaves with mixed green and greyed-green lower surfaces and acute shaped leaf tips.

'ANTHERBI' differs from the commercial variety 'ANTHCOZAM' (unpatented) in that 'ANTHERBI' has white flowers, immature spadix that are yellow-orange and cataphyll that are green and greyed-red at the apex, whereas 'ANTHCOZAM' has orange-red flowers, immature spadix that are orange and cataphyll that are greyed-red. Additionally, 'ANTHERBI' has red spathes that are flat, whereas 'ANTHCOZAM' has dark red spathes that are wavy.

'ANTHERBI' differs from commercial variety 'ANTHEPEDI' (U.S. Plant Pat. No. 18,644) in that 'ANTHERBI' has elliptical cordate shaped leaves and spathes that are flat, whereas 'ANTHEPEDI' has ovate cordate shaped leaves and spathes that are cupped. Additionally, 'ANTHERBI' has cataphyll that are green and greyed-red at the apex, whereas 'ANTHEPEDI' has cataphyll that are light green.

I claim:

1. A new and distinct variety of *Anthurium* plant named 'ANTHERBI', substantially as illustrated and described herein.

* * * * *